(12) United States Patent
Frost et al.

(10) Patent No.: US 8,853,450 B2
(45) Date of Patent: Oct. 7, 2014

(54) NITRILE HYDRATION CATALYZED BY RECYCLABLE RUTHENIUM COMPLEXES

(71) Applicant: Board of Regents of the Nevada System of Higher Education, on behalf of the University of Nevada, Reno, Reno, NV (US)

(72) Inventors: Brian J. Frost, Reno, NV (US); Wei-Chih Lee, Taipei (TW)

(73) Assignee: Board of Regents of the Nevada System of Higher Education, on behalf of the University of Nevada, Reno, Reno, NV (US)

(*) Notice: Subject to any disclaimer, the term of this patent is extended or adjusted under 35 U.S.C. 154(b) by 26 days.

(21) Appl. No.: 13/654,895

(22) Filed: Oct. 18, 2012

(65) Prior Publication Data

US 2013/0096344 A1 Apr. 18, 2013

Related U.S. Application Data

(60) Provisional application No. 61/548,333, filed on Oct. 18, 2011.

(51) Int. Cl.
*C07C 231/06* (2006.01)
*C07D 213/81* (2006.01)

(52) U.S. Cl.
CPC ............... *C07C 231/065* (2013.01); *C07D 213/81* (2013.01)
USPC ........................................ 564/126

(58) Field of Classification Search
CPC ...................................... C07C 231/06
USPC ........................................... 564/126
See application file for complete search history.

(56) References Cited

U.S. PATENT DOCUMENTS 6,133,478 A * 10/2000 Parkins et al. ............ 564/126

OTHER PUBLICATIONS

Cadierno et al., "Bis(allyl)ruthenium(IV) Complexes Containing Water-Soluble Phosphane Ligands: Synthesis, Structure, and Application as Catalysts in the Selective Hydration of Organonitriles into Amides," Chem. Eur. J. 16:9808-9817, 2010.
Cadierno et al., "Selective Ruthenium-Catalyzed Hydration of Nitriles to Amides in Pure Aqueous Medium Under Neutral Conditions," Chem. Eur. J. 14:6601-6605, 2008.
García-Álvarez et al., "Arene-Ruthenium(II) Complexes Containing Amino-Phosphine Ligands as Catalysts for Nitrile Hydration Reactions," Organometallics. 29:3955-3965, 2010.
García-Álvarez et al., "Ibuprofenamide: a convenient method of synthesis by catalytic hydration of 2-(4-isobutylphenyl)propionitrile in pure aqueous medium," Tetrahedron Letters. 52:4218-4220, 2011.
García-Garrido et al., "Chemistry by Nanocatalysis: First Example of a Solid-Supported RAPTA Complex for Organic Reactions in Aqueous Medium," ChemSusChem. 4:104-111, 2011.

* cited by examiner

*Primary Examiner* — Shailendra Kumar

(57) ABSTRACT

A method for hydrating a nitrile derivative to generate an amide derivative is provided. The method includes mixing the nitrile derivative with a ruthenium catalyst complex in an aqueous solution to form a mixture, and reacting the nitrile derivative with water in the aqueous solution and in the presence of the ruthenium catalyst complex to form a reacted mixture comprising the amide derivative. The ruthenium catalyst complex is represented by the following structural formula: $RuX_2(L)_n$, wherein X is an anionic ligand, L is a bifunctional phosphine ligand, and n is 3 or 4.

20 Claims, No Drawings

NITRILE HYDRATION CATALYZED BY RECYCLABLE RUTHENIUM COMPLEXES

RELATED APPLICATIONS

This application claims the benefit of U.S. Provisional Application Ser. No. 61/548,333, filed on Oct. 18, 2011, which is hereby incorporated by reference herein in its entirety.

GOVERNMENT GRANT SUPPORT CLAUSE

This invention was made with government support under grant #CHE-0645365 awarded by the National Science Foundation. The government has certain rights in the invention.

FIELD OF THE INVENTION

The present invention relates generally to methods for catalytically converting nitriles to amides, and more particularly to catalytic methods for aqueous phase nitrile hydration reactions.

BACKGROUND OF THE INVENTION

Amides are versatile and important synthetic intermediates used in the production of a variety of plastics, detergents, lubricants, and polymers. Traditional methods of hydrating nitriles to amides involve the use of strong bases or acids, enzymes, or heterogenous catalysts, but these traditional methods suffer from various drawbacks.

For example, strong acids or bases are generally used in stoichiometric excess (e.g., 96% $H_2SO_4$ or 50% KOH/t-BuOH) under harsh conditions, which often induces further hydrolysis of the desired amides to carboxylic acids thereby lowering the yield thereof. Moreover, poor tolerance for other functional groups is often observed under such harsh acidic or basic conditions. While performed under much milder conditions, enzymes are often sensitive to the variation in structure of the nitriles and the reaction conditions. Moreover, slow reaction rates, low conversions, and reproducibility are common problems encountered with enzymatic reactions. Heterogeneous catalysts, such as zeolites and metal oxides, often produce poor yields and demonstrate poor tolerance for other functional groups.

Transition metal complexes offer a potential alternative to the traditional approaches. A variety of transition metal complexes have been developed as catalysts for nitrile hydration in organic media, but many of these transition metal complexes are often air-sensitive and/or non-recyclable catalysts.

Accordingly, new catalytic methods or processes for the conversion of nitriles to amides that overcome one or more of the deficiencies of the traditional approaches are needed.

SUMMARY OF THE INVENTION

Certain aspects of the present disclosure are described in the appended claims. There are additional features and advantages of the subject matter described herein. They will become apparent as this specification proceeds. In this regard, it is to be understood that the claims serve as a brief summary of varying aspects of the subject matter described herein. The various features described in the claims and below for various embodiments may be used in combination or separately. For example, specified ranges may be inclusive of their recited endpoints, unless explicitly excluded. Any particular embodiment need not provide all features noted above, nor solve all problems or address all issues noted above.

According to embodiments of the present invention, a method for hydrating a nitrile derivative to generate an amide derivative is provided. The method includes mixing the nitrile derivative with a ruthenium catalyst complex in an aqueous solution to form a mixture, and reacting the nitrile derivative with water in the aqueous solution and in the presence of the ruthenium catalyst complex to form a reacted mixture comprising the amide derivative. The ruthenium complex is represented by a structural formula: $RuX_2(L)_n$, wherein X is an anionic ligand; L is a bifunctional phosphine ligand, and n is 3 or 4.

DETAILED DESCRIPTION

Unless otherwise explained, all technical and scientific terms used herein have the same meaning as commonly understood by one of ordinary skill in the art to which this disclosure belongs. In case of conflict, the present specification, including explanations of terms, will control. The singular terms "a," "an," and "the" include plural referents unless context clearly indicates otherwise. Similarly, the word "or" is intended to include "and" unless the context clearly indicates otherwise. The term "comprising" means "including;" hence, "comprising A or B" means including A or B, as well as A and B together.

Aspects of the invention are directed to methods for the hydration of nitrile derivatives to their corresponding amides in an aqueous solution in the presence of, and catalyzed by, a ruthenium catalyst complex represented by a structural formula $RuX_2(L)_n$, where X is an anionic ligand; L is a bifunctional phosphine ligand, and n is 3 or 4. According to one embodiment, the anionic ligand is selected from the group consisting of Cl, Br, I, H, hydroxide, alkoxide, carboxylate (e.g., acetate), and combinations thereof. According to another embodiment, n is 4. The conversion of nitrile derivatives to their corresponding amide is shown in Scheme (I) below:

Scheme (I)

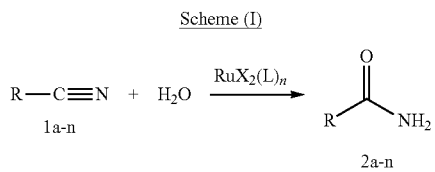

According to embodiments of the present invention, the ruthenium catalyst complex is an air-stable, water-soluble, and recyclable ruthenium (Ru) catalyst. According to an embodiment, the ruthenium catalyst complex may be introduced to the aqueous solution in a previously prepared form. For example, the ruthenium catalyst complex may be provided as a stable complex, or a hydrate or solvate thereof. Alternatively, the ruthenium catalyst complex may be prepared in situ by the combination of a suitable ruthenium compound and the desired bifunctional phosphine ligand, as discussed further below.

The ruthenium compounds suitable for preparing the ruthenium catalyst complexes described herein are not particularly limited. For example, exemplary ruthenium compounds, include ruthenium (III) compounds such as halide salts, e.g., $RuCl_3$, $RuBr_3$, $RuI_3$, or $RuF_3$, ruthenium (III) acetate, or ruthenium (III) acetylacetonate, ruthenium phosphate, ruthenium nitrate, or ruthenium sulfate; and ruthenium (II) compounds such as RuX$_2$(PRR'R'')$_n$, where X is Cl, Br, I, H, hydroxide, alkoxide, carboxylate, or combinations thereof; where R, R', and R'' are independently selected from substituted or unsubstituted alkyl or aryls; and n is an integer equal to 3 or 4. The hydrates and solvates are also suitable.

To form the ruthenium catalyst complex, the ruthenium compound is mixed with the appropriate bifunctional phosphine ligand in a suitable solvent. As used herein, a bifunctional phosphine ligand includes a phosphine compound (PRR'R'')$_n$ that optionally comprises one or more heteroatom substituents on R, R', and/or R''. Exemplary bifunctional phosphine ligands include, but are not limited to, 1,3,5-triaza-7-phosphaadamantane (3, PTA) and derivatives thereof, P(CH$_2$OH)$_3$, P(CH$_2$CH$_2$CH$_2$OH)$_3$, triphenylphosphine trissulfonate (TPPTS), triphenylphosphine monosulfolate (TPPMS), P(CH$_2$NH$_2$)$_3$, P(CH$_2$NH$_3$Br)$_3$, and P(CH$_2$NH$_3$Cl)$_3$. Exemplary PTA-derivatives include, but are not limited to, PTA-CR$^1$R$^2$NHR$^3$ (3a), PTA-CR$^4$NR$^5$ (3b), PTA-CR$^6$NR$^7$ (3c), PTA-CR$^8$R$^9$OH (3d), PTA-CO$_2$M (3e), PTA-PR$^{10}$R$^{11}$ (3f), where R$^1$, R$^2$, R$^3$, R$^4$, R$^5$, R$^6$, R$^7$, R$^8$, R$^9$, R$^{10}$, or R$^{11}$ can be H, or substituted or unsubstituted alkyls, aryls, alkaryls, or heteroaryls; and M is an alkali metal such as sodium or lithium.

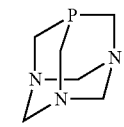

3

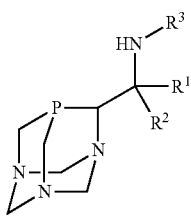

3a

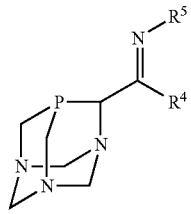

3b

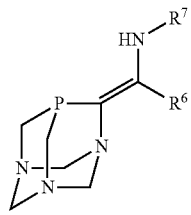

3c

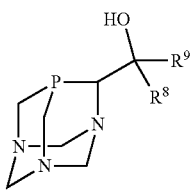

3d

-continued

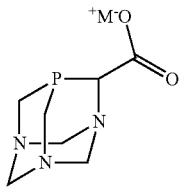

3e

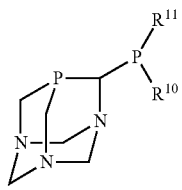

3f

According to one aspect, when forming the ruthenium complex catalyst in situ, a stoichiometric ratio between the ruthenium compound and the bifunctional phosphine ligand is in a range from about 1:1 to about 1:10. In another embodiment, the stoichiometric ratio is in the range from about 1:4 to about 1:6.

Suitable solvents useful for preparing the ruthenium catalyst complexes include water, buffered aqueous solutions, and organic solvents such as ethanol. According to embodiments wherein the ruthenium catalyst complexes are formed in situ, the aqueous solution, which includes water, a buffered aqueous solution, or biphasic aqueous solutions that include immiscible organic solvents, are amenable.

According to one example, the ruthenium catalyst complex is RuCl$_2$(PTA)$_4$, which can be prepared in situ by refluxing an ethanolic solution of ruthenium (III) chloride and 6 equivalents of 1,3,5-triaza-7-phosphaadamantane (PTA).

The structure of the nitrile derivatives amenable to the catalytic hydrolysis described herein is not particularly limited. Accordingly, suitable nitrile derivatives, defined by the general formula R—CN (1), where R can be a substituted or unsubstituted aryl or heteroaryl; or a substituted or unsubstituted alkyl or alkenyl, which include, but are not limited to, benzonitrile, 2-methylbenzonitrile, 3-methylbenzonitrile, 4-methylbenzonitrile, 4-methoxybenzonitrile, 4-nitrobenzonitrile, 4-bromobenzonitrile, 4-hydroxybenzonitrile, 2-cyanopyridine, heptyl cyanide, pivalonitrile, and acrylonitrile.

According to embodiments of the invention, catalyzed hydration of the nitrile derivatives to their corresponding amide derivatives is conducted in an aqueous reaction medium or solution, such as water, a buffered aqueous solution, or biphasic aqueous solution. According to one aspect, the pH of the aqueous solution has a value greater than about 4. For example, the pH of the aqueous solution may be in a range from about 4 to about 12, from about 4 to about 10, from about 5 to about 10, from about 6 to about 10, from about 7 to about 10, from about 5 to about 9, or from about 6 to about 8. The pH of the aqueous solution may be buffered using a buffered aqueous solution, such as a phosphate, a sulfate, a carbonate, or a bicarbonate buffer system. According to one aspect, the aqueous solution may further include an immiscible organic solvent thereby forming a biphasic aqueous solution, where upon cessation of mixing, the immiscible organic solvent and the aqueous solution can separate into discernable layers. An exemplary organic solvent suitable for forming biphasic aqueous solutions is tert-amyl alcohol.

According to one aspect of the present invention, the hydration of nitrile derivatives is carried out at temperatures greater than room temperature. According to one embodiment, the mixture is heated to a temperature greater than 50° C. For example, the ruthenium catalyst complex catalyzed hydration of nitriles to amides may be conducted at a temperature in a range from about 50° C. to about reflux temperature of the mixture, which is dependent upon the pressure of the reaction mixture environment. Accordingly, for reactions run at ambient pressure, the temperature may be in the range from about 50° C. to about 100° C., or from about 75° C. to about 100° C. Of course, if the nitrile hydrolysis reaction is performed under a pressurized atmosphere, temperatures exceeding the ambient pressure reflux temperature can be realized.

According to embodiments of the present invention, the ruthenium catalyst complexes are air stable complexes, at room temperature and at the elevated reaction temperatures, which obviates the requirement and costs associated with establishing and maintaining an inert atmosphere for the catalytic nitrile hydration reaction. As used herein, characterization of the ruthenium catalyst complex as being "air stable and recyclable" means that the ruthenium catalyst complex can be recycled in a nitrile hydration reaction under air conditions at least three times without demonstrating greater than a 10% decrease in catalytic activity, as measured by percent conversion at 24 hours at 100° C. Accordingly, another aspect of embodiments of the invention is that the methods may be performed using recycled ruthenium catalyst complexes.

After achieving a desired level of conversion of the nitrile derivative to its corresponding amide derivative, the amide derivative may be isolated from the reacted mixture by precipitation or extraction. According to one embodiment, the temperature of the reacted mixture is decreased to a level wherein a solid form of the amide derivative forms and precipitates from the aqueous solution. The solid form of the amide derivative may be isolated from its supernatant by filtering or decanting after centrifugation. According to another embodiment, the amide derivative may be isolated by extracting the amide derivate from the aqueous solution containing the reacted mixture with an immiscible organic solvent, in which the amide derivative is substantially soluble. In this embodiment, the immiscible organic solvent is mixed with the aqueous solution to extract the amide derivative into the immiscible organic solvent. And upon standing, separate layers of immiscible organic solvent and aqueous solution form thereby permitting separation of the immiscible organic solvent layer containing the amide derivative from the aqueous solution, which still contains the recyclable ruthenium catalyst complex. The amide derivative can be separated from the immiscible organic solvent by precipitation and/or distillation.

Non-limiting examples, in accordance with various principles of the present invention, are described below.

EXAMPLES

All manipulations were performed in air. Solvents (water, tert-amyl alcohol, toluene) were used as received without further purification or degassing. Benzonitrile, o-tolunitrile, m-tolunitrile, p-tolunitrile, p-methoxybenzonitrile, p-cyanophenol, p-nitrobenzonitrile, p-bromobenzonitrile, p-cyanobenzaldehyde, 2-cyanopyridine, 4-methylbenzyl cyanide, heptyl cyanide, pivalonitrile, acrylonitrile, ruthenium trichloride trihydrate, and deuterated NMR solvents were obtained from commercial sources and used as received. 1,3,5-Triaza-7-phosphaadamantane (PTA), [RuCl$_2$($\eta^6$-toluene)]$_2$, and [RuCl$_2$(PTA)$_4$] were synthesized as reported in the literature. See Daigle, D. J.; Pepperman, A. B., Jr.; Vail, S. L. *J. Heterocycl. Chem.* 1974, 11, 407-408; Bennett, M. A.; Smith, A. K. *J. Chem. Soc., Dalton. Trans.* 1974, 233-241; D. J. Darensbourg, F. Joó, M. Kannisto, A. Katho, J. H. Reibenspies and D. J. Daigle, *Inorg. Chem.*, 1994, 13, 200-208, respectively. GC/MS analyses were obtained using a Varian CP 3800 GC (DB5 column) equipped with a Saturn 2200 MS and a CP 8410 auto-injector or an Agilent 7890A GC equipped with an Agilent 5975C inert MSD with triple axis detector and an Agilent 7693 autosampler. NMR spectra were recorded on a Varian NMR System 400 spectrometer with chemical shifts reported in ppm. $^1$H and $^{13}$C NMR spectra were referenced to residual solvent relative to tetramethylsilane (TMS). Phosphorus chemical shifts are relative to an external reference of 85% H$_3$PO$_4$ in D$_2$O with positive values downfield of the reference.

General Procedure for the Catalytic Nitrile Hydration.

Under air, 1 mmol nitrile, 3 mL water, and 5 mol % [RuCl$_2$(PTA)$_4$] (40 mg) were added to a Telfon®-sealed screw-cap culture tube and stirred at 100° C. for 7 h. The GC yields were obtained by taking a small aliquot (~50 μL) from the hot solution and extracting with CH$_2$Cl$_2$ (2 mL×3) and analyzing by GC-MS. Isolated yields were obtained by either decanting the aqueous layer from the product crystals or by evaporation of the solvent followed by column chromatography over silica gel using ethyl acetate as eluent. The identity of the resulting amides was assessed by comparison of their $^1$H and $^{13}$C{$^1$H} NMR spectroscopic data with those reported in the literature and by their retention time and fragmentation from GC/MS with that of an authentic sample.

Generally the resulting amide derivatives (2a-2n, Scheme 1) crystallized out from water after hydration. However, in some cases the product did not precipitate out of aqueous solution in appreciable quantity. In the cases where isolated yield by decantation was <60%, the reaction mixture was evaporated to dryness and purified by column chromatography. Purification by column chromatography: Benzamide (a), m-toluamide (c), p-hydroxybenzamide, p-nitrobenzamide (f), 4-formylbenzamide (h), picolinamide, octamide, pivalamide, acrylamide. After the general procedure, the solvent was removed under reduced pressure. The resulting crude product was purified by column chromatography over silica gel using ethyl acetate as eluent yielding a white solid. Purification by decantation: o-Toluamide (b), p-toluamide (d), p-methoxybenzamide (e), p-bromobenzamide (g), 2-(p-tolyl)-acetamide (i). After the general procedure, the reaction tube was cooled to RT and placed in a refrigerator for about one hour. The amide crystals were filtered and washed with cold water (5 mL×3) to give a white solid.

Catalyst Recycling Experiments in Water.

Under air, the corresponding nitrile (1 mmol), water (3 mL), and the ruthenium catalyst [RuCl$_2$(PTA)$_4$] (5 mol %) were introduced into a Telfon®-sealed screw-cap culture tube, and the reaction mixture was stirred at 100° C. for 7 hours. The conversion (GC yield) was obtained by taking a small aliquot (~50 μL) from the hot solution, which after extraction with CH$_2$Cl$_2$ (2 mL×3) was analyzed by GC-MS. After reaction completion, the solution was allowed to cool to room temperature and then placed in a refrigerator overnight, during which time the amide precipitated from solution. The aqueous supernatant containing catalyst was transferred to another reaction tube by syringe, fresh nitrile was added, and the tube heated to 100° C. for the next hydration cycle. A small amount of cold water (~0.3 mL) was used to rinse the amide crystals and was transferred to the new tube to maximize catalyst recovery.

Example 1

The catalytic activity of 5 mol % [RuCl$_2$(PTA)$_4$] toward nitrile hydration was evaluated in aqueous solution at 100° C. with 1 mmol nitrile in a culture tube under air (Scheme 2).

Scheme 2: [RuCl$_2$(PTA)$_4$]-catalyzed nitrile hydration

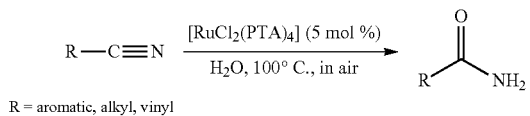

R = aromatic, alkyl, vinyl

Under the conditions described here, RuCl$_3$ (5 mol %) provided a 54% conversion of benzonitrile to benzamide in 24 hours. Benzonitrile hydration by 2 mol % RuCl$_3$ was previously reported to yield 28% benzamide after 3 h at 130° C. No hydration was observed in the absence of a catalyst, or with PTA, [RuCl$_2$(η$^6$-toluene)]$_2$, or [RuCl$_2$(PPh$_3$)$_3$] as catalysts. Benzonitrile hydration by [RuCl$_2$(PTA)$_4$] did not occur at 50° C. and provided only 23% conversion after 24 h at 75° C. The hydration of benzonitrile catalyzed by [RuCl$_2$(PTA)$_4$] showed a >99% conversion to benzamide at 100° C. after 7 hours, in contrast to the inactive [RuCl$_2$(PPh$_3$)$_3$], potentially demonstrating a cooperative effect of the nitrogen-containing PTA versus PPh$_3$. For comparison, nitrile hydration catalyzed by 5 mol % [RuCl$_2$(η$^6$-arene)(PTA)] (η$^6$-arene=benzene, p-cymene, 1,3,5-trimethylbenzene, and hexamethylbenzene), showed >98% conversions in 4-9 h for aqueous benzonitrile hydration under N$_2$ at 100° C. An in situ generated catalyst formed by the addition of RuCl$_3$ hydrate with 6 equivalence of PTA provided results similar to the preformed complex RuCl$_2$PTA$_4$ (Table 1).

The conversion of various nitriles (1a-1n) to the corresponding amides (2a-2n) was explored with results summarized in Table 1. All nitriles were efficiently converted to amides with 67-99% conversion in 7 hours and >99% conversions by 24 hours, with the exception of 2-cyanopyridine (1j, 81% after 24 h). After completion, the reaction was cooled to 0° C. and, in most cases, the product amides crystallized out as white needles and were easily isolated in 67-81% yield by decantation. Identity of the isolated amides (2a-2n) was confirmed by GC-MS and NMR spectroscopy.

TABLE 1

Substrate scope for nitrile hydration catalyzed by [RuCl$_2$(PTA)$_4$].[a] or RuCl$_3$ hydrate + 6 PTA.[a]

| | | RuCl$_2$(PTA)$_4$ | | RuCl$_3$ + 6 PTA | |
|---|---|---|---|---|---|
| Entry | Substrate | Conversion[b] (%) | Isolated yield (%) | Conversion[b] (%) | Isolated yield (%) |
| 1a | ⌬—CN | 99 | 91[c] | 99 | 93[c] |
| 1b | 2-CH$_3$-C$_6$H$_4$-CN | 83(99) | 67[d] | 98 | 94[d] |
| 1c | 3-CH$_3$-C$_6$H$_4$-CN | 96(99) | 84[c] | 98 | 83[c] |
| 1d | 4-CH$_3$-C$_6$H$_4$-CN | 97(99) | 77[d] | 98 | 82[d] |
| 1e | 4-CH$_3$O-C$_6$H$_4$-CN | 90(99) | 78[d] | 86(99) | 85[d] |
| 1f | 4-HO-C$_6$H$_4$-CN | 89(99) | 90[c] | 32(99) | 91[c] |
| 1g | 4-O$_2$N-C$_6$H$_4$-CN | 99 | 86[c] | 98 | 89[c] |
| 1h | 4-Br-C$_6$H$_4$-CN | 99 | 73[d] | 34(95) | 81[d] |

TABLE 1-continued

Substrate scope for nitrile hydration catalyzed by [RuCl$_2$(PTA)$_4$],[a] or RuCl$_3$ hydrate + 6 PTA.[a]

| | | RuCl$_2$(PTA)$_4$ | | RuCl$_3$ + 6 PTA | |
|---|---|---|---|---|---|
| Entry | Substrate | Conversion[b] (%) | Isolated yield (%) | Conversion[b] (%) | Isolated yield (%) |
| 1i | OHC—⌬—CN | 99 | 87[c] | ND[e] | ND[e] |
| 1j | pyridyl-CN | 43(81) | 72[c] | 11(57) | 49[c] |
| 1k | H$_3$C—⌬—CN | 99 | 81[d] | ND[e] | ND[e] |
| 1l | heptyl-CN | 72(99) | 88[c] | 13(78) | 69[c] |
| 1m | t-Bu-CN | 67(99) | 85[c] | ND[e] | ND[e] |
| 1n | CH$_2$=CH-CN | 99 | 87[c] | 82(99) | 17[c] |

[a]Conditions: nitrile (1 mmol), [RuCl$_2$(PTA)$_4$] (5 mol %), H$_2$O (3 mL), 100° C., in air.
[b]GC yields of amide (2a-2n) after 7 h (24 h yield in parentheses).
[c]Isolated by column chromatography.
[d]Isolated by decantation.
[e]not determined.

Substituted benzonitriles bearing electron-withdrawing groups (Table 1 above, entries 1g-1i) exhibited slightly more efficient conversions to amides than those with electron-donating groups (entries 1b-1f). Presumably, the presence of the electron-withdrawing group makes the nitrile carbon more susceptible to nucleophilic attack by an activated water molecule. As previously reported for ortho-substituted benzonitriles, o-tolunitrile exhibited lower conversion relative to m- and p-tolunitriles (Table 1, entries 1b-1d), which is attributed to steric hindrance of the o-tolunitriles. Hydration of 4-cyanobenzaldehyde led to 4-formylbenzamide in a 99% conversion in 7 h with an intact formyl moiety (entry 1i). The coordinating ability of the pyridyl functionality reduced catalytic activity as hydration of 2-cyanopyridine to picolinamide resulted in only 81% conversion after 24 h (entry 1j).

[RuCl$_2$(PTA)$_4$] was also effective as a hydration catalyst for the less reactive aliphatic nitriles (Table 1, entries 1k-1m). 4-Methylbenzyl cyanide was transformed with 99% conversion in 7 hours (entry 1k) into the amide. Hydration of the sterically bulky pivalonitrile (1m) to pivalamide proceeded with a 99% conversion in 24 h although a modest conversion of 67% was observed after 7 h (entry 1m). The resistance of tertiary nitriles toward hydrolysis has been noted. The industrially important acrylonitrile was almost quantitatively converted into acrylamide in 7 hours without observation of polymerization or hydrolysis byproducts (Table 1, entry 1n). For all the nitrile hydrations studied, the corresponding amides were the only product observed (no carboxylic acids were detected by GC-MS). Thus, the catalytic conditions described here are compatible with ether (entry 1e), hydroxyl (entry 1f), nitro (entry 1g), bromo (entry 1h), formyl (entry 1i), pyridyl (entry 1j), benzyl (entry 1k), alkyl (entries 1l-1m), and olefinic (entry 1n) functional groups, which establishes a wide synthetic scope.

Nitrile hydration catalyzed by RuX$_2$(PR$_3$)$_3$, RuX$_2$(PR$_3$)$_4$, and in situ generated catalysts (RuCl$_3$XH$_2$O+nPR$_3$), where X is selected from the group consisting of Cl, Br, I, H, hydroxide, alkoxide, carboxylate, and combinations thereof; PR$_3$ is selected from the group consisting of 1,3,5-triaza-7-phosphaadamantane (PTA), P(CH$_2$OH)$_3$, P(CH$_2$CH$_2$CH$_2$OH)$_3$, P(CH$_2$NH$_2$)$_3$, P(CH$_2$NH$_3$Br)$_3$, P(CH$_2$NH$_3$Cl)$_3$, PTA-CO$_2$Li, triphenylphosphine monosulfonate (TPPMS), and triphenylphosphine trissulfonate (TPPTS) also work in water and in the presence of phosphate buffer at a variety of pH ranges. The activity for benzonitrile hydration by [RuCl$_2$(PTA)$_4$] in phosphate buffer with pH 5.9-11.7 was much higher than the catalytic activity in water alone (See Table 2 below).

TABLE 2

Effect of the pH value on the hydration of benzonitrile catalyzed by [RuCl$_2$(PTA)$_4$].[a]

| | With [RuCl$_2$(PTA)$_4$][c] | | | Without [RuCl$_2$(PTA)$_4$][c] | | |
|---|---|---|---|---|---|---|
| | 2 h | 7 h | 24 h | 2 h | 7 h | 24 h |
| DI water | 67 | 99 | — | 0 | 0 | — |
| pH 4.9[b] | 21 | 77 | 99 | 0 | 0 | — |
| pH 5.9[b] | 86 | 99 | — | — | — | — |
| pH 6.8[b] | 99 | — | — | 0 | 0 | — |
| pH 11.7[b] | 96 | — | — | 90 | 93[d] | — |

[a]Conditions: nitrile (1 mmol), [RuCl$_2$(PTA)$_4$] (5 mol %), H$_2$O (3 mL), 100° C., 7 h, in air.
[b]Phosphate buffer solutions.
[c]Conversions are determined by GC.
[d]With formation of 3% acid.

The activity for benzonitrile hydration in water is similar to the activity in buffer having a pH of about 5.5 consistent with the observation that an aqueous solution of [RuCl$_2$(PTA)$_4$]

has a pH of about 5 to about 5.5. No activity was observed in pH 4.9, 5.9 and 6.8 buffers without catalyst. At pH 11.7, in the absence of catalyst, hydration proceeded with formation of benzoic acid, likely be due to catalysis by the hydroxide present at pH 11.7. In the presence of catalyst no benzoic acid was observed even in pH 11.7 buffer.

Little or no induction period was observed in the reaction kinetics of the hydration of benzonitrile by [RuCl$_2$(PTA)$_4$] in water under the following reaction conditions: benzonitrile (1 mmol), [RuCl$_2$(PTA)$_4$] (5 mol %), H$_2$O (3 mL), 100° C., in air. Free PTA was observed in solution while monitoring the reaction by GC-MS, which suggests that formation of the catalytically active species may involve PTA dissociation, presumably followed by nitrile coordination. $^{31}$P{$^1$H} NMR spectroscopy was obtained on reaction mixtures after 2 h in attempt to identify active species in water. The NMR spectra were consistent with a series of substitutional isomers [Ru(PTA)$_x$(H$_2$O)$_y$(PhCN)$_{6-x-y}$]$^{2+}$ similar to the results of others from reaction of [Ru(H$_2$O)$_6$]$^{2+}$ with PTA and cis/trans isomerization of [RuCl$_2$(PTA)$_4$]. A short induction period was observed in nitrile hydration reactions carried out with an in situ generated catalyst made by addition of RuCl$_3$ and 6 PTA to the reaction solution.

The durability of [RuCl$_2$(PTA)$_4$] also was evaluated by reducing the catalyst loading (See Table 3 below). The catalyst loading was examined down to 0.001 mol % for the hydration of benzonitrile. Turnover numbers (TONs) up to 22000 (entry 9, Table 3) were obtained. Preparative scale reactions were also examined for the hydration of benzonitrile (Table 3, entries 5, 7, 8). For example, 2.02 grams of benzonitrile was hydrated at 0.1 mol % catalyst loading to give a 2.25 g (93%) isolated benzamide with a TON of 930 and a TOF of 30 h$^{-1}$ (Table 3, entry 5). When carried out in pH 6.8 buffer TOF greater than 130 h$^{-1}$ have been observed for benzonitrile hydration by [RuCl$_2$PTA$_4$]. The TOF increases with a decrease in catalyst loading or increase in nitrile. For example, in Table 3 entries 4 and 5, the benzonitrile concentration is increased from 0.33 M to 6.66 M at 0.1 mol % catalyst loading and the TOF increases from 14.1 to 30 h$^{-1}$. Faster reactions with higher concentration of the nitrile have been observed in other ruthenium catalytic systems. It should be noted that in the preparative scale reactions (2 mL benzonitrile, 3 mL water) two phases were observed during hydration followed by formation of a homogeneous solution, indicating hydration was complete. The rate of hydration was also found to increase with an increase in the volume of water (i.e. dilution) possibly indicative of substrate/product inhibition at higher concentration (See Table 4 below). Addition of 1 mmol (100 mol %, 0.33 M) NaCl to the hydration of benzonitrile resulted in a slight decrease in conversion from 99 to 93% after 7 hours.

TABLE 3

Effect of reduced catalyst loading on the hydration of benzonitrile catalyzed by [RuCl$_2$(PTA)$_4$].[a]

| Entry | Catalyst (mol %) | Time (h) | Conv.[b] (%) | TON[c] | TOF[d] (h$^{-1}$) |
|---|---|---|---|---|---|
| 1 | 5 | 7 | 99 | 19.8 | 2.8 |
| 2 | 1 | 7 | 87 | 87 | 12.4 |
| 3 | 1 | 24 | 99 | 99 | 4.1 |
| 4 | 0.1 | 70 | 99 | 990 | 14.1 |
| 5[e] | 0.1 | 31 | 98(93)[f] | 930[g] | 30[g] |
| 6 | 0.01 | 504 | 66 | 6600 | 13.1 |
| 7[e] | 0.01 | 528 | (83)[h] | 8300[g] | 15.7[g] |
| 8[e] | 0.001 | 864 | (12)[h] | 12000[g] | 13.9[g] |
| 9 | 0.001 | 2328 | (22)[h] | 22000[g] | 9.5[g] |

[a]Conditions: nitrile (1 mmol, 0.33M), H$_2$O (3 mL), 100° C., in air.
[b]Determined by GC (isolated yields in parentheses).
[c]TON (mol product)/(mol catalyst).
[d]TOF (mol product)/(mol catalyst)/h.
[e]Nitrile (20 mmol, 6.66M in water), H$_2$O (3 mL).
[f]Isolated yield by recrystallization from water (2.12 g, 88%) and purification of the filtrate by chromatography providing an additional 0.13 g (5%) benzamide.
[g]Based on isolated yield.
[h]Isolated yield by column chromatography.

TABLE 4

Effect of dilution on the hydration of benzonitrile at 1 mol % catalyst loading.[a]

| Entry | H$_2$O (mL) | [Nitrile] (M) | Conversion[b] (%) | | |
|---|---|---|---|---|---|
| | | | 2 h | 7 h | 24 h |
| 1 | 1 | 1.00 | 19 | 62 | 99 |
| 2 | 3 | 0.33 | 41 | 92 | 99 |
| 3 | 5 | 0.20 | 43 | 96 | 99 |

[a]Conditions: nitrile (1 mmol), [RuCl$_2$(PTA)$_4$] (1 mol %), 100° C., in air.
[b]Conversions are determined by GC.

Further evidence for the robust nature of the catalyst was obtained upon storing an aqueous solution of [RuCl$_2$(PTA)$_4$] under air for four weeks at ~0° C. Hydration of benzonitrile performed using the stored aqueous solution of [RuCl$_2$(PTA)$_4$] (1 mol % loading) resulted in a 83% conversion after 7 hours compared to 87% by freshly-prepared catalyst in water; both reactions reached >99% conversion by 24 hours.

The ability to store aqueous solutions of [RuCl$_2$(PTA)$_4$] prompted exploring the reusability of the catalyst through recycling experiments with benzonitrile and 4-methylbenzyl cyanide (See Table 5 below). After 7 hours, the reaction was cooled overnight and the aqueous supernatant containing the catalyst was carefully transferred to another reaction tube followed by addition of fresh nitrile. The precipitated amide product was collected and washed with cold water. Further purification was unnecessary as determined by GC-MS, $^1$H and $^{13}$C{$^1$H} NMR spectroscopy. The isolated yields in Table 5 below were obtained by decantation; maximized isolated yields (93%) can be obtained by extraction with an organic solvent (Table 5, run 1$^c$). Recycling was carried out at least seven times without significant loss of the catalytic activity or selectivity in the case of benzonitrile. With 4-methylbenzyl cyanide a decrease in activity was observed after the fifth recycling experiment. This is attributed to incomplete catalyst recovery during transfer of the aqueous supernatant indicated by a faint yellow color observed in the product. The fine solid product made complete transfer of the aqueous catalyst supernatant difficult, resulting in the lower conversion.

TABLE 5

Recycling experiments with [RuCl$_2$(PTA)$_4$] under aqueous conditions.[a]

| Substrate | Recycling Experiment[b] | | | | | | |
|---|---|---|---|---|---|---|---|
| | 1 | 2 | 3 | 4 | 5 | 6 | 7 |
| benzonitrile (PhCN) | 99(18)[c] | 99(53) | 99(67) | 99(55) | 99(61) | 99(52) | 99(66) |
| 4-methylbenzyl cyanide (H$_3$C-C$_6$H$_4$-CH$_2$CN) | 99(69) | 99(80) | 99(92) | 96(85) | 95(89) | 85(87) | 38 |

[a]Conditions: nitrile (1 mmol), [RuCl$_2$(PTA)$_4$] (5 mol %), H$_2$O (3 mL), 100° C., 7 h, in air.
[b]Conversions are determined by GC (isolated yields by decantation are given in parentheses).
[c]A 93% isolated yield can be obtained by extraction with CH$_2$Cl$_2$ (3 mL × 5).

The isolated yields in the aqueous phase recycling experiments with benzonitrile were modest as decantation left some benzamide dispersed in water. Aqueous/organic biphasic hydration of benzonitrile was thus also studied (See Table 6 below). Due to the mixing efficiency of two phases, aqueous biphasic hydration of benzonitrile to benzamide reached 84% conversion after 7 hours compared to 99% conversion in water; therefore, 24 hours was used in the biphasic reactions. After 24 hours the organic phase (tert-amyl alcohol) was decanted off and benzamide isolated. Fresh benzonitrile and tert-amyl alcohol were added to the aqueous phase for the next reaction. The catalyst could be recycled five times without significant loss of catalytic activity. A slight decrease in catalytic activity was observed after the fifth cycle attributed to catalyst leaching into the organic layer (slight yellow color observed over time in the organic layer). Ruthenium leaching into the organic layer was indeed observed by ICP-AES with the [Ru] increasing with each cycle: recycling experiment 1 (2.9 ppm Ru), 4 (24.5 ppm Ru), and 7 (77.2 ppm Ru).

Catalyst Recycling Experiments in an Aqueous/Organic Biphasic System

Under air, the corresponding nitrile (1 mmol), water (1.5 mL), tert-amyl alcohol (1.5 mL), and the ruthenium catalyst [RuCl$_2$(PTA)$_4$] (5 mol %) were introduced into a Telfon®-sealed screw-cap culture tube, and the reaction mixture was stirred at 100° C. for 24 hours and allowed to cool to room temperature and placed in a refrigerator for one hour. The reaction was monitored by taking aliquots from the organic layer followed by dilution with CH$_2$Cl$_2$ and analysis by GC-MS. After reaction completion, toluene (2 mL) was added to this biphasic media followed by cooling the tube to ~0° C. for one hour. The isolation of benzamide was performed by decanting the organic layer and evaporating to dryness to afford clean product. The organic layers of runs 1, 4 and 7 were examined by ICP-AES analysis. The results are shown in Table 6 below.

TABLE 6

Biphasic hydration of benzonitrile with [RuCl$_2$(PTA)$_4$] recycling experiments and leaching of ruthenium into the organic layer determined by ICP-AES.[a]

| Substrate | | Trial | Recycling experiment[b] | | | | |
|---|---|---|---|---|---|---|---|
| | | 1 | 2 | 3 | 4 | 5 | 6 | 7 |
| PhCN | 1[c] | 99 | | 99 | 99 | 98 | | 98 | 89 | 88 |
| PhCN | 2[c] | 99 (2.9)[e] | | 99 | 99 | 98 (24.5)[e] | | 90 | 88 | 82 (77.2)[e] |
| PhCN | 3[d] | 99 (58.3)[e] | | 99 | 99 | 94 (150.7)[e] | | 83 | 78 | 76 (125.2)[e] |

[a]Conditions: nitrile (1 mmol), [RuCl$_2$(PTA)$_4$] (5 mol %), H$_2$O (1.5 mL), tert-amyl alcohol (1.5 mL), 100° C., 24 h, in air.
[b]% conversion determined by GC.
[c]With addition of toluene.
[d]Without addition of toluene.
[e][Ru] (in ppm) in organic layer determined by ICP-AES.

Accordingly, an efficient and recyclable catalytic system to convert nitriles to amides in aqueous environments with tolerance of air and a variety of functional groups is described hereinabove. Advantages of the catalytic system include easy catalyst preparation, simple reaction setup, and the use of green solvent (water). The catalyst is robust and highly recyclable under atmospheric conditions (no inert atmosphere required). Isolation of many amides by decantation from water largely decreases or circumvents the use of organic solvents, even in the workup steps. The gram-scale amide synthesis by hydration of nitriles using [RuCl$_2$(PTA)$_4$] in water is simple, practical and environmentally friendly.

While the invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative product and/or method and examples shown and described. The various features of exemplary embodiments described herein may be used in any combination. Accordingly, departures may be made from such details without departing from the scope of the general inventive concept.

What is claimed is:

1. A method for hydrating a nitrile derivative to generate an amide derivative comprising:

mixing the nitrile derivative with a ruthenium catalyst complex in an aqueous solution to form a mixture, the ruthenium catalyst complex represented by the following structural formula:

$RuX_2(L)_n$, wherein X is an anionic ligand, L is a bifunctional phosphine ligand, and n is either 3 or 4; and reacting the nitrile derivative with water in the aqueous solution and in the presence of the ruthenium catalyst complex to form a reacted mixture comprising the amide derivative.

2. The method of claim 1, wherein the bifunctional phosphine ligand is selected from the group consisting of 1,3,5-triaza-7-phosphaadamantane (PTA) or derivatives thereof, $P(CH_2OH)_3$, $P(CH_2CH_2CH_2OH)_3$, triphenylphosphine trissulfonate (TPPTS), triphenylphosphine monosulfolate (TPPMS), $P(CH_2NH_2)_3$, $P(CH_2NH_3Br)_3$, and $P(CH_2NH_3Cl)_3$.

3. The method of claim 1, wherein the bifunctional phosphine ligand is 1,3,5-triaza-7-phosphaadamantane (PTA) or a PTA derivative.

4. The method of claim 1, wherein the anionic ligand is selected from the group consisting of Cl, Br, I, H, hydroxide, alkoxide, carboxylate, and combinations thereof.

5. The method of claim 1, wherein the ruthenium catalyst complex is $RuCl_2(PTA)_4$, where PTA is 1,3,5-triaza-7-phosphaadamantane.

6. The method of claim 1, wherein the aqueous solution is selected from the group consisting of water, a buffered aqueous solution, and a biphasic aqueous solution.

7. The method of claim 1, wherein the aqueous solution has a pH greater than about 4.

8. The method of claim 1, wherein the aqueous solution has a pH in a range from about 4 to about 10.

9. The method of claim 1, further comprising heating the mixture to a temperature greater than 50° C.

10. The method of claim 1, further comprising heating the mixture to a temperature in a range from about 50° C. to about 100° C.

11. The method of claim 1, further comprising:
forming the ruthenium catalyst complex in situ by mixing a ruthenium compound with the bifunctional phosphine ligand in the aqueous solution.

12. The method of claim 11, wherein the ruthenium compound is selected from the group consisting $RuCl_3$, $RuBr_3$, $RuI_3$, $RuF_3$, ruthenium (III) acetate, ruthenium (III) acetylacetonate; ruthenium phosphate, ruthenium nitrate, ruthenium sulfate, $RuX_2(PRR'R")_n$, wherein X is selected from the group consisting of Cl, Br, I, H, hydroxide, alkoxide, carboxylate, and combinations thereof wherein R, R', and R" are independently selected from substituted or unsubstituted alkyl or aryls; and n is an integer equal to 3 or 4; and solvates and/or hydrates thereof.

13. The method of claim 11, wherein the ruthenium compound is a halide salt.

14. The method of claim 11, wherein a stoichiometric ratio between the ruthenium compound and the bifunctional phosphine ligand is in a range from about 1:1 to about 1:10.

15. The method of claim 14, wherein the stoichiometric ratio is in the range from about 1:4 to about 1:6.

16. The method of claim 1, wherein reacting the nitrile derivative with water in the aqueous solution and in the presence of the ruthenium catalyst complex is conducted in the presence of air to form the amide derivative.

17. The method of claim 1, further comprising:
isolating the amide derivative from the reacted mixture.

18. The method of claim 17, wherein isolating the amide derivative from the reacted mixture comprises:
lowering a temperature of the reacted mixture to induce precipitation of a solid form of the amide derivative; and
filtering the solid form of the amide derivative.

19. The method of claim 17, wherein isolating the amide derivative from the reacted mixture comprises:
mixing an immiscible organic solvent with the aqueous solution to extract the amide derivative from the aqueous solution; and
separating the immiscible organic solvent containing the extracted amide derivative from the aqueous solution.

20. The method of claim 1, further comprising recycling the ruthenium catalyst complex.